United States Patent
Wang

(10) Patent No.: US 10,870,615 B2
(45) Date of Patent: *Dec. 22, 2020

(54) COMPOSITIONS CONTAINING 2-CHLORO-1,1,1,2-TETRAFLUOROPROPANE (HCFC-244BB)

(71) Applicant: Honeywell International Inc., Morris Plains, NJ (US)

(72) Inventor: Haiyou Wang, Amherst, NY (US)

(73) Assignee: Honeywell International Inc., Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/279,542

(22) Filed: Feb. 19, 2019

(65) Prior Publication Data

US 2019/0210945 A1    Jul. 11, 2019

Related U.S. Application Data

(63) Continuation of application No. 15/864,722, filed on Jan. 8, 2018, now Pat. No. 10,246,389.

(51) Int. Cl.
    *C07C 19/10*    (2006.01)
(52) U.S. Cl.
    CPC .................................. *C07C 19/10* (2013.01)
(58) Field of Classification Search
    CPC ....... C07C 19/10; C07C 17/389; C07C 21/18; C07C 17/206; C07C 17/395; C09K 50/45; C09K 5/044
    See application file for complete search history.

(56) References Cited

U.S. PATENT DOCUMENTS

| | | | |
|---|---|---|---|
| 7,803,283 B2 | 9/2010 | Pham et al. | |
| 8,058,486 B2 | 11/2011 | Merkel et al. | |
| 8,697,923 B2 | 4/2014 | Smith et al. | |
| 8,766,020 B2 | 7/2014 | Wang et al. | |
| 8,975,454 B2 | 3/2015 | Merkel et al. | |
| 9,296,670 B2 | 3/2016 | Wang et al. | |
| 9,758,450 B2 | 9/2017 | Wang et al. | |
| 10,246,389 B1 | 4/2019 | Wang | |
| 2009/0256110 A1 | 10/2009 | Merkel et al. | |
| 2010/0187088 A1 | 7/2010 | Merkel et al. | |
| 2011/0031436 A1 | 2/2011 | Mahler et al. | |
| 2012/0037843 A1* | 2/2012 | Pham | C07C 17/38 252/79.3 |
| 2012/0184785 A1 | 7/2012 | Cottrell et al. | |
| 2014/0303413 A1* | 10/2014 | Merkel | C07C 17/389 570/179 |
| 2015/0251033 A1* | 9/2015 | Nappa | C09K 3/00 51/296 |
| 2017/0166500 A1 | 6/2017 | Merkel et al. | |

FOREIGN PATENT DOCUMENTS

| | | |
|---|---|---|
| EP | 2634166 A2 | 9/2013 |
| GB | 2547277 A | 8/2017 |
| WO | 2015/092211 A1 | 6/2015 |
| WO | 2017013405 A1 | 1/2017 |
| WO | 2017066603 A1 | 4/2017 |

OTHER PUBLICATIONS

U.S. Appl. No. 62/416,206, filed Nov. 2, 2016, 17 pages.
International Search Report and Written Opinion received for PCT Patent Application No. PCT/US2019/012615, dated Apr. 29, 2019, 9 pages.

* cited by examiner

*Primary Examiner* — Jafar F Parsa
(74) *Attorney, Agent, or Firm* — Faegre Drinker Biddle & Reath LLP

(57) ABSTRACT

The present disclosure provides various compositions including 2-chloro-1,1,1,2-tetrafluoropropane (HCFC-244bb) and at least one impurity comprising 2,3,3,3-tetrafluoropropene (HFO-1234yf), pentafluoropropene (HFO-1225ye isomer(s)), 1,3,3,3-tetrafluoropropene (HFO-1234ze isomer(s)), 1,1,1,2,2-pentafluoropropane (HFC-245cb), 1,1,1,2-tetrafluoropropane (HFC-254eb), 2-chloro-3,3,3-trifluoropropene (HCFO-1233xf), 1-chloro-1,1,2,2-tetrafluoropropane (HCFC-244cc), chlorotetrafluoropropene (HCFO-1224 isomers), E-1-chloro-3,3,3-trifluoropropene (HCFO-1233zdE), 1,1,1,3,3-pentafluoropropane (HFC-245fa), heptafluorobutane (HFC-347 isomers), 2-chloro-1,1,1,3,3-pentafluoropropane (HFC-235da), 3-chloro-1,1,1,2-tetrafluoropropane (HCFC-244eb), 3-chloro-3,3,3-trifluoropropane (HCFC-253fb), dichlorotrifluoropropene (HCFO-1223 isomers), 2,3-dichloro-1,1,1,2-tetrafluoropropane (HCFC-234bb), 2,2-dichloro-1,1,1-trifluoropropane (HCFC-243db), chlorohexafluorobutene (HFO-1326 isomers), hexafluorobutene (HFO-1336 isomers), pentafluorobutene (HFO-1345 isomers), heptafluorobutene (HFO-1327 isomers), tetrafluorohexane (HFC-5-11-4 isomers), 1,3,3,3-tetrafluoropropane (HFC-254fb), chlorohexafluorobutane (HFC-346 isomers), octafluoropentane (HFC-458 isomers), octafluorohexene, 2,2-dichloro-1,1,1-trifluoroethane (HCFC-123), (Z)-1-chloro-3,3,3-trifluoropropene (HCFO-1233zd(Z)), $C_5H_2F_{10}$ isomer, $C_6H_2F_8$ isomer, $C_6H_4F_8$ isomers, decafluorobutane ($C_4F_{10}$), $C_6H_3F_7$ isomer, $C_6H_3F_9$ isomer, dichlorodifluoropropene (HCFO-1232 isomers), trichlorotrifluoropropane (HCFC-233 isomers), $C_6H_3Cl_2F_7$ isomers, trichlorodifluoropropane (HCFC-242 isomers), $C_8H_3F_7$ isomers, or long-chain halogenated hydrocarbons having a boiling point above about 15° C.

20 Claims, 4 Drawing Sheets

COMPOSITIONS CONTAINING 2-CHLORO-1,1,1,2-TETRAFLUOROPROPANE (HCFC-244BB)

CROSS REFERENCE TO RELATED APPLICATION

This application is a Continuation of U.S. patent application Ser. No. 15/864,722, filed Jan. 8, 2018, which is herein incorporated by reference in its entirety.

FIELD OF THE DISCLOSURE

This disclosure relates to compositions that contain 2-chloro-1,1,1,2-tetrafluoropropane (HCFC-244bb) and at least one impurity. Such compositions are useful for various purposes, such as for the production of 2,3,3,3-tetrafluoropropene (HFO-1234yf or 1234yf) and similar compounds.

BACKGROUND

Hydrofluoroolefins (HFOs), such as tetrafluoropropenes are known effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Due to suspected environmental problems associated with the use of some of these fluids, including the relatively high global warming potentials associated therewith, it is desirable to use fluids having the lowest possible global warming potential (GWP) in addition to also having zero ozone depletion potential (ODP). Thus, there is considerable interest in developing environmentally friendlier materials for the applications mentioned above.

HFOs having zero ozone depletion and low global warming potential have been identified as potentially filling this need. However, the toxicity, boiling point, and other physical properties of such chemicals vary greatly from isomer to isomer. One HFO having valuable properties is 2,3,3,3-tetrafluoropropene (HFO-1234yf or 1234yf).

HFO-1234yf has been shown to be a low global warming compound with low toxicity and, thus, can meet increasingly stringent requirements for refrigerants in mobile air conditioning. Accordingly, compositions containing HFO-1234yf are among the materials being developed for use in many of the aforementioned applications.

Various methods are known for producing HFO-134yf, such as those described in U.S. Pat. No. 8,058,486, entitled INTEGRATED PROCESS TO PRODUCE 2,3,3,3-TETRAFLUOROPROPENE issued on Nov. 15, 2011, U.S. Pat. No. 8,975,454, entitled PROCESS FOR PRODUCING 2,3,3,3-TETRAFLUOROPROPENE issued on Mar. 10, 2015, and U.S. Pat. No. 8,766,020, entitled PROCESS FOR PRODUCING 2,3,3,3-TETRAFLUOROPROPENE issued on Jul. 1, 2014, all of which are herein incorporated by reference in their entirety.

Because the production of 2,3,3,3-tetrafluoropropene may potentially be subject many undesirable side reactions, compositions and methods that allow for the improved yields, more economical processes, and limited waste production in the production of 2,3,3,3-tetrafluoropropene and subsequent processes are needed.

SUMMARY

The present disclosure provides various manufacturing processes and compositions that contain 2-chloro-1,1,1,2-tetrafluoropropane (HCFC-244bb) and at least one impurity. Such compositions may be useful for the production of 2,3,3,3-tetrafluoropropene (HFO-1234yf or 1234yf). Such methods and compositions may allow for the acceptable yields, sufficiently economical processes, and acceptable levels of waste production in the manufacture of HFO-1234yf.

Such compositions may include compositions including HCFC-244bb and at least one impurity comprising at least one impurity comprising 2,3,3,3-tetrafluoropropene (HFO-1234yf), pentafluoropropene (HFO-1225ye isomer(s)), 1,3,3,3-tetrafluoropropene (HFO-1234ze isomer(s)), 1,1,1,2,2-pentafluoropropane (HFC-245cb), 1,1,1,2-tetrafluoropropane (HFC-254eb), 2-chloro-3,3,3-trifluoropropene (HCFO-1233xf), 1-chloro-1,1,2,2-tetrafluoropropane (HCFC-244cc), chlorotetrafluoropropene (HCFO-1224 isomers), E-1-chloro-3,3,3-trifluoropropene (HCFO-1233zdE), 1,1,1,3,3-pentafluoropropane (HFC-245fa), heptafluorobutane (HFC-347 isomers), 2-chloro-1,1,1,3,3-pentafluoropropane (HFC-235da), 3-chloro-1,1,1,2-tetrafluoropropane (HCFC-244eb), 3-chloro-3,3,3-trifluoropropane (HCFC-253fb), dichlorotrifluoropropene (HCFO-1223 isomers), 2,3-dichloro-1,1,1,2-tetrafluoropropane (HCFC-234bb), 2,2-dichloro-1,1,1-trifluoropropane (HCFC-243db), chlorohexafluorobutene (HFO-1326 isomers), hexafluorobutene (HFO-1336 isomers), pentafluorobutene (HFO-1345 isomers), heptafluorobutene (HFO-1327 isomers), tetrafluorohexane (HFC-5-11-4 isomers), 1,3,3,3-tetrafluoropropane (HFC-254fb), chlorohexafluorobutane (HFC-346 isomers), octafluoropentane (HFC-458 isomers), octafluorohexene, 2,2-dichloro-1,1,1-trifluoroethane (HCFC-123), (Z)-1-chloro-3,3,3-trifluoropropene (HCFO-1233zd(Z)), $C_5H_2F_{10}$ isomer, $C_6H_2F_8$ isomer, $C_6H_4F_8$ isomers, decafluorobutane ($C_4F_{10}$), $C_6H_3F_7$ isomer, $C_6H_3F_9$ isomer, dichlorodifluoropropene (HCFO-1232 isomers), trichlorotrifluoropropane (HCFC-233 isomers), $C_6H_3Cl_2F_7$ isomers, trichlorodifluoropropane (HCFC-242 isomers), $C_8H_3F_7$ isomers, or long-chain halogenated hydrocarbons having a boiling point above about 15° C.

In various embodiments, the at least one impurity may present in an amount from about 0.0001 wt. % to about 2 wt. %, in an amount from about 0.0005 wt. % to about 0.5 wt. %, or in an amount from about 0.001 wt. % to about 0.05 wt. %.

In some embodiments, the composition comprises at least two different impurities. For example, in some embodiments, the at least two different impurities may include a first impurity and the first impurity is 253fb. In some embodiments, one impurity may be heptafluorobutane, such as 1,1,1,2,2,3,3-heptafluorobutane. In some embodiments, such as those with 253fb and heptafluorobutane, the combined amount of the 253fb and the heptafluorobutane is present in an amount between 0.0005 wt. % to 0.5 wt. %, between 0.001 wt. % to 0.2 wt. %, or between 0.0015 wt. % to 0.12 wt. %.

BRIEF DESCRIPTION OF THE DRAWINGS

The above mentioned and other features and objects of this disclosure, and the manner of attaining them, will become more apparent and the disclosure itself will be better understood by reference to the following description of exemplary embodiments of the disclosure taken in conjunction with the accompanying drawings, wherein.

Figure 1A:
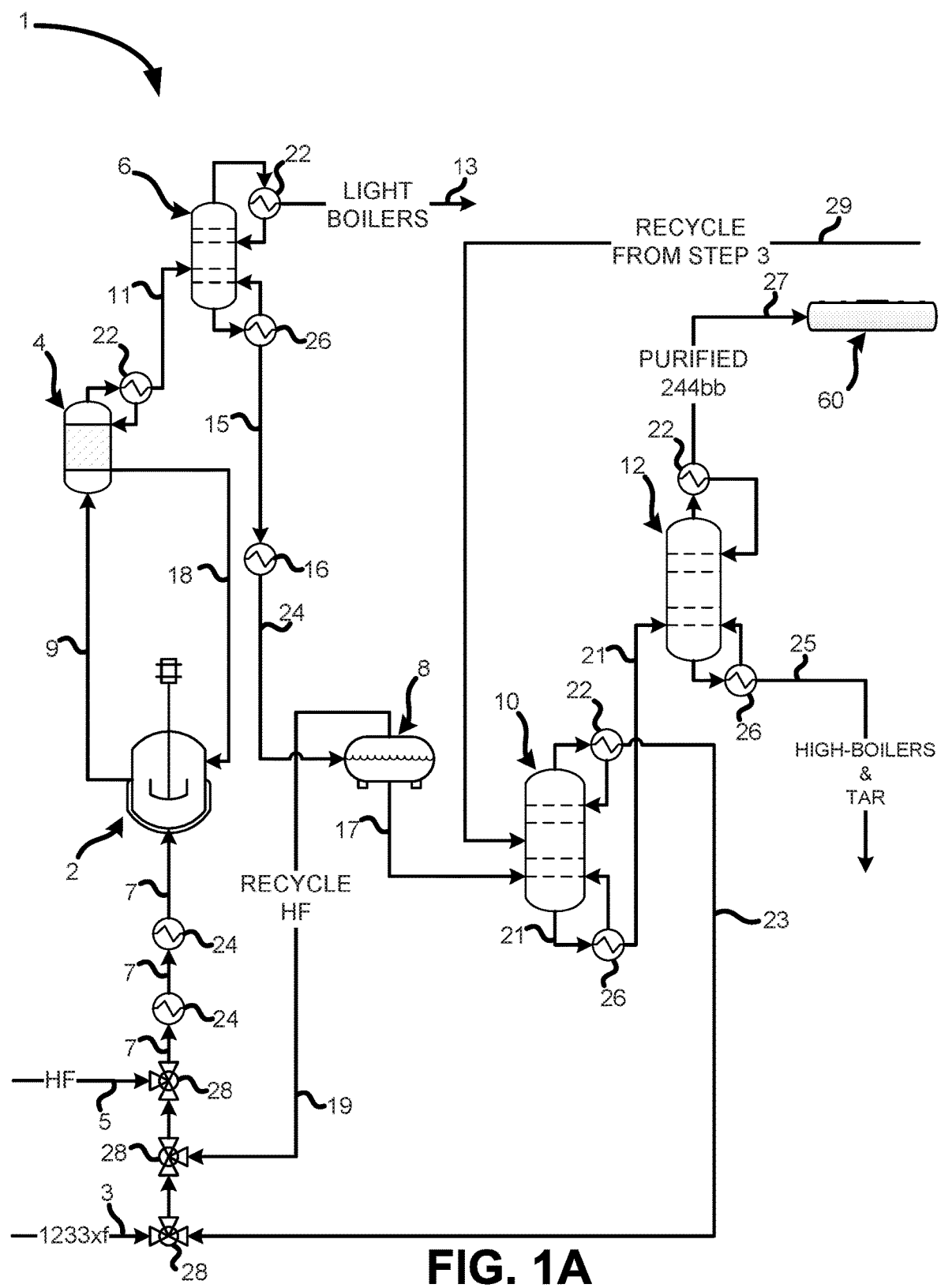
FIG. 1A is a process flow diagram showing an exemplary portion of a manufacturing process of 2,3,3,3-tetrafluoropropene (HFO-1234yf)

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplification set out herein illustrates exemplary embodiments of the disclosure, in various forms, and such exemplifications are not to be construed as limiting the scope of the disclosure in any manner.

DETAILED DESCRIPTION

As briefly described above, this disclosure provides various compositions that are suitable for the manufacture of 2,3,3,3-tetrafluoropropene (HFO-1234yf or 1234yf). The manufacture of HFO-1234yf from 1,1,2,3-tetrachloropropene (TCP) and hydrogen fluoride can be generalized in a three step process.

Step 1 can be understood as producing 2-chloro-3,3,3-trifluoropropene (HCFO-1233xf) from 1,1,2,3-tetrachloropropene (1230xa) in a vapor phase reactor according to the following reaction scheme:

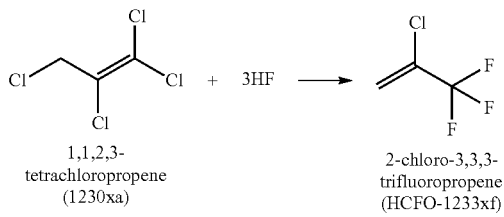

1,1,2,3-tetrachloropropene (1230xa)

2-chloro-3,3,3-trifluoropropene (HCFO-1233xf)

Step 2 can be understood as producing 2-chloro-1,1,1,2-tetrafluoropropane (HCFC-244bb) from 2-chloro-3,3,3-trifluoropropene (HCFO-1233xf) in a reactor, such as a liquid phase reactor, according to the following reaction scheme:

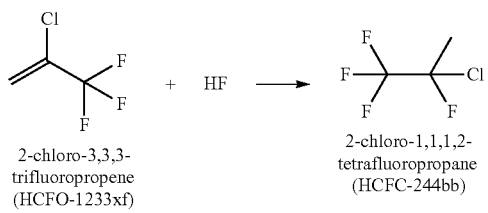

2-chloro-3,3,3-trifluoropropene (HCFO-1233xf)

2-chloro-1,1,1,2-tetrafluoropropane (HCFC-244bb)

Step 3 can be understood as producing 2,3,3,3-tetrafluoropropene (HFO-1234yf) from 2-chloro-1,1,1,2-tetrafluoropropane (HCFC-244bb) in a reactor, such as a vapor phase reactor according to the following reaction scheme:

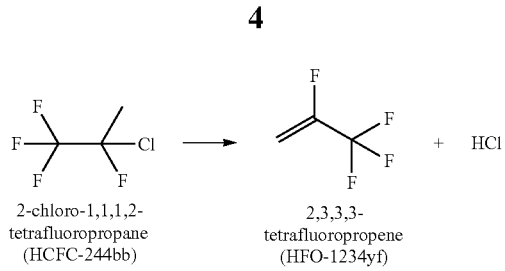

2-chloro-1,1,1,2-tetrafluoropropane (HCFC-244bb)

2,3,3,3-tetrafluoropropene (HFO-1234yf)

Not wishing to be bound by or to any particular theory of operation, certain aspects of the present disclosure are based on the observation and understanding that, during certain dehydrochlorination reactions (during Step 3) of certain dehydrochlorination starting materials, such as 2-chloro-1,1,1,2-tetrafluoropropane (HCFC-244bb), to produce 2,3,3,3-tetrafluoropropene (HFO-1234yf), the presence of 2-chloro-3,3,3-trifluoropropene (HCFO-1233xf) in the reaction starting materials, such as HCFC-244bb feedstock, can lead to dramatically reduced conversion of HCFC-244bb to HFO-1234yf and increased formation of 3,3,3-trifluoropropyne ($CF_3CCH$), which is the dehydrochlorinated product of 2-chloro-3,3,3-trifluoropropene (HCFO-1233xf).

These results are disadvantageous from the standpoint of a reduced yield of the desired product. Also, with respect to the formation of 3,3,3-trifluoropropyne ($CF_3CCH$) byproduct, same is further disadvantageous in that same is a flammable gas and toxic, and thus undesired.

For example, the presence of 3-chloro-1,1,1-trifluoropropane (HCFC-253fb or 253fb) in the reactor for Step 3 may result in the formation and/or presence of elevated levels of both 3,3,3-trifluoropropene (HFO-1243zf or 1243zf) and vinyl chloride (1140), which may be subsequently found in 1234yf crude product. The presence of the 1243zf and 1140 impurities can result in extra yield loss during final purification steps and is thus undesired due to the difficulty of separating 1243zf and 1140 from 1234yf.

Also, the presence of high boilers and tars (which are long-chain halogenated hydrocarbons) formed as side-reactions in the reactor of Step 3 appears to either cause excessive coking of the Step 3 reactor or contribute to it, resulting in premature deactivation of the reactor. Non-limiting examples of high boilers include, but are not limited to, $C_4F_{10}$, $C_5H_2F_{10}$ isomers, various tetrafluorohexane isomers, $C_6H_3F_7$ isomers, $C_6H_3Cl_2F_7$ isomers, $C_6H_2F_8$ isomers, $C_6H_4F_8$ isomers, $C_6H_3F_9$ isomers, various octafluorohexene isomers, and $C_8H_3F_7$ isomers. These high boilers may further react to form tar, which can be condensed to form a dark brown or black viscous liquid upon cooling.

Figure 2:
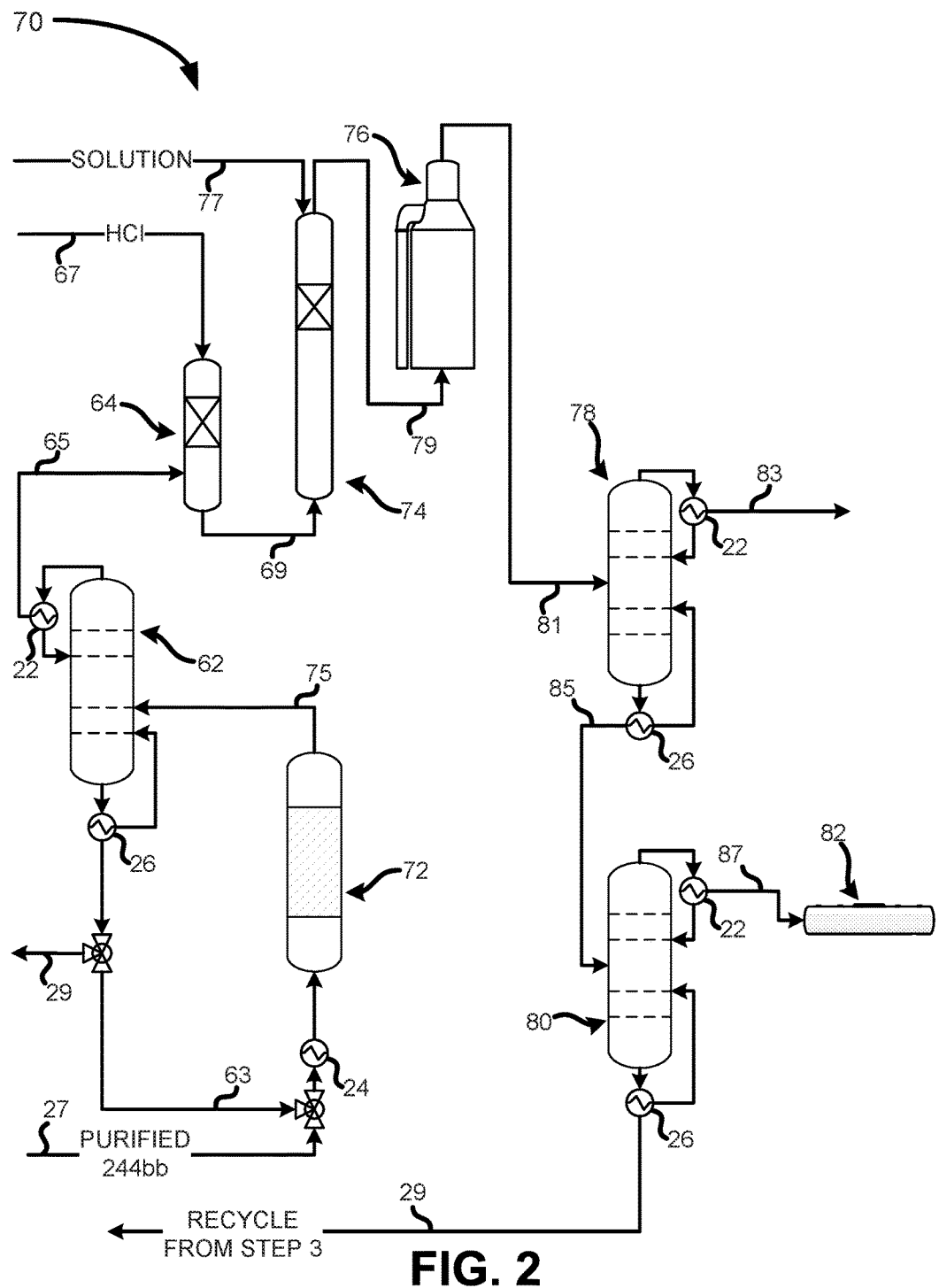
FIG. 2 is a process flow diagram depicting Step 3 of an exemplary process of manufacturing HFO-1234yf.

However, the presence of some impurities prior to dehydrochlorinating of Step 3 (such as shown in FIG. 2 as dehydrochlorinating reactor 72) may yield an acceptable economical process. It has been unexpectedly found that the compositions disclosed herein, containing HCFC-244bb and particular impurities may be suitable starting compositions for Step 3 even though some impurities are present. Non-limiting examples of such impurities include 1-chloro-1,1,2,2-tetrafluoropropane (HCFC-244cc), E-1-chloro-3,3,3-trifluoropropene (HCFO-1233zdE), and heptafluorobutane (HFC-347 isomers).

The embodiments disclosed below are not intended to be exhaustive or limit the disclosure to the precise form disclosed in the following detailed description. Rather, the embodiments are chosen and described so that others skilled in the art may utilize their teachings.

Compositions useful as a feedstock for Step 3 may include 2-chloro-1,1,1,2-tetrafluoropropane (HCFC-244bb) and at least one impurity comprising at least one of 2,3,3,3-tetrafluoropropene (HFO-1234yf), pentafluoropropene (HFO-1225ye isomer(s)), 1,3,3,3-tetrafluoropropene (HFO-1234ze isomer(s)), 1,1,1,2,2-pentafluoropropane (HFC-245cb), 1,1,1,2-tetrafluoropropane (HFC-254eb), 2-chloro-3,3,3-trifluoropropene (HCFO-1233xf), 1-chloro-1,1,2,2-tetrafluoropropane (HCFC-244cc), chlorotetrafluoropropene (HCFO-1224 isomers), E-1-chloro-3,3,3-trifluoropropene (HCFO-1233zdE), 1,1,1,3,3-pentafluoropropane (HFC-245fa), heptafluorobutane (HFC-347 isomers), 2-chloro-1,1,1,3,3-pentafluoropropane (HFC-235da), 3-chloro-1,1,1,2-tetrafluoropropane (HCFC-244eb), 3-chloro-3,3,3-trifluoropropane (HCFC-253fb), dichlorotrifluoropropene (HCFO-1223 isomers), 2,3-dichloro-1,1,1,2-tetrafluoropropane (HCFC-234bb), 2,2-dichloro-1,1,1-trifluoropropane (HCFC-243db), chlorohexafluorobutene (HFO-1326 isomers), hexafluorobutene (HFO-1336 isomers), pentafluorobutene (HFO-1345 isomers), heptafluorobutene (HFO-1327 isomers), tetrafluorohexane (HFC-5-11-4 isomers), 1,3,3,3-tetrafluoropropane (HFC-254fb), chlorohexafluorobutane (HFC-346 isomers), octafluoropentane (HFC-458 isomers), octafluorohexene, 2,2-dichloro-1,1,1-trifluoroethane (HCFC-123), (Z)-1-chloro-3,3,3-trifluoropropene (HCFO-1233zd(Z)), $C_5H_2F_{10}$ isomers, $C_6H_2F_8$ isomers, $C_6H_4F_8$ isomers, decafluorobutane ($C_4F_{10}$), $C_6H_3F_7$ isomers, $C_6H_3F_9$ isomers, dichlorodifluoropropene (HCFO-1232 isomers), trichlorotrifluoropropane (HCFC-233 isomers), $C_6H_3Cl_2F_7$ isomer, trichlorodifluoropropane (HCFC-242 isomers), $C_8H_3F_7$ isomers, or tars (which are long-chain halogenated hydrocarbons).

For example, a composition containing 244bb may also have one or more of the impurities discussed below. Such compositions may have HCFC-244bb present in an amount of at least 95.0 wt. %, at least 97 wt. %, or at least 98 wt. %, and as high as 99.9995 wt. %, as high as 99.0000 wt. %, or 98.1 wt. %, or any combination thereof, such as between 95.0 wt. % and 99.9995 wt. %, between 97 wt. % and 99.0000 wt. %, between 95.0 wt. % and 98.1 wt. %, or between 98.0 wt. % and 99.0 wt. %.

In particular, 253fb may be present in an amount of at least 0.0001 wt. %, at least 0.0005 wt. %, at least 0.001 wt. %, and at least 0.0015 wt. %, and as high as 0.05 wt. %, as high as 0.03 wt. %, as high as 0.02 wt. %, as high as 0.01 wt. %, as high as 0.005 wt. %, or any combination thereof, such as 0.0001 wt. % to 0.05 wt. %, 0.0001 wt. % to 0.03 wt. %, 0.0005 wt. % to 0.02 wt. %, 0.001 wt. % to 0.01 wt. %, or 0.0015 wt. % to 0.005 wt. %.

In the foregoing compositions, the total sum of light components non-exclusively including 2,3,3,3-tetrafluoropropene (HFO-1234yf), pentafluoropropene (HFO-1225ye isomer(s)), 1,3,3,3-tetrafluoropropene (HFO-1234ze isomer(s)), 1,1,1,2,2-pentafluoropropane (HFC-245cb), 1,1,1,2-tetrafluoropropane (HFC-254eb) may be at least 0.0005 wt. %, at least 0.001 wt. %, and at least 0.0015 wt. %, and as high as 0.5 wt. %, as high as 0.2 wt. %, as high as 0.1 wt. %, as high as 0.05 wt. %, as high as 0.01 wt. %, or any combination thereof, such as 0.0005 wt. % to 0.5 wt. %, 0.0005 wt. % to 0.2 wt. %, 0.0005 wt. % to 0.1 wt. %, 0.001 wt. % to 0.05 wt. %, or 0.0015 wt. % to 0.01 wt. %.

HCFC-1233xf may be present in an amount of at least 0.05 wt. %, at least 0.1 wt. %, and at least 0.2 wt. %, and as high as 5.0 wt. %, as high as 3.0 wt. %, as high as 2.0 wt. %, or any combination thereof, such as 0.05 wt. % to 5.0 wt. %, 0.1 wt. % to 3.0 wt. %, or 0.2 wt. % to 2.0 wt. %.

HCFC-244cc may be present in an amount of at least 0.0005 wt. %, at least 0.001 wt. %, and at least 0.0015 wt. %, and as high as 0.5 wt. %, as high as 0.2 wt. %, as high as 0.1 wt. %, or any combination thereof, such as 0.0005 wt. % to 0.5 wt. %, 0.001 wt. % to 0.2 wt. %, or 0.0015 wt. % to 0.1 wt. %.

HCFO-1224 may be present in an amount of at least 0.0001 wt. %, at least 0.0002 wt. %, and at least 0.0003 wt. %, and as high as 0.01 wt. %, as high as 0.005 wt. %, as high as 0.003 wt. %, as high as 0.002 wt. %, or any combination thereof, such as 0.0001 wt. % to 0.01 wt. %, 0.0001 wt. % to 0.005 wt. %, 0.0002 wt. % to 0.003 wt. %, or 0.0003 wt. % to 0.002 wt. %.

HCFO-1233zdE may be present in an amount of at least 0.0001 wt. %, at least 0.0002 wt. %, and at least 0.0005 wt. %, and as high as 0.05 wt. %, as high as 0.02 wt. %, as high as 0.01 wt. %, or any combination thereof, such as 0.0001 wt. % to 0.05 wt. %, 0.0002 wt. % to 0.02 wt. %, or 0.0005 wt. % to 0.01 wt. %.

HFC-245fa may be present in an amount of at least 0.0005 wt. %, at least 0.001 wt. %, and at least 0.0015 wt. %, and as high as 1.0 wt. %, as high as 0.5 wt. %, as high as 0.1 wt. %, as high as 0.05 wt. %, as high as 0.01 wt. %, or any combination thereof, such as 0.0005 wt. % to 1.0 wt. %, 0.0005 wt. % to 0.5 wt. %, 0.0005 wt. % to 0.1 wt. %, 0.001 wt. % to 0.05 wt. %, or 0.0015 wt. % to 0.01 wt. %.

In some embodiments, HFC-347 isomers may be present in an amount of at least 0.0005 wt. %, at least 0.001 wt. %, and at least 0.0015 wt. %, and as high as 0.5 wt. %, as high as 0.2 wt. %, as high as 0.1 wt. %, as high as 0.05 wt. %, as high as 0.02 wt. %, or any combination thereof, such as 0.0005 wt. % to 0.5 wt. %, 0.0005 wt. % to 0.2 wt. %, 0.001 wt. % to 0.05 wt. %, or 0.0015 wt. % to 0.02 wt. %.

HCFC-235da may be present in an amount of at least 0.0001 wt. %, at least 0.0005 wt. %, and at least 0.001 wt. %, and as high as 0.02 wt. %, as high as 0.01 wt. %, as high as 0.005 wt. %, as high as 0.003 wt. %, as high as 0.002 wt. %, or any combination thereof, such as 0.0001 wt. % to 0.02 wt. %, 0.0001 wt. % to 0.01 wt. %, 0.0005 wt. % to 0.005 wt. %, or 0.001 wt. % to 0.003 wt. %.

HCFC-244eb may be present in an amount of at least 0.0001 wt. %, at least 0.0005 wt. %, and at least 0.001 wt. %, and as high as 0.05 wt. %, as high as 0.03 wt. %, as high as 0.02 wt. %, as high as 0.01 wt. %, as high as 0.005 wt. %, or any combination thereof, such as 0.0001 wt. % to 0.05 wt. %, 0.0001 wt. % to 0.03 wt. %, 0.0001 wt. % to 0.02 wt. %, 0.0005 wt. % to 0.01 wt. %, or 0.001 wt. % to 0.005 wt. %.

HCFC-234bb may be present in an amount of at least 0.0001 wt. %, at least 0.0005 wt. %, and at least 0.001 wt. %, and as high as 0.1 wt. %, as high as 0.05 wt. %, as high as 0.03 wt. %, as high as 0.02 wt. %, as high as 0.01 wt. %, or any combination thereof, such as 0.0001 wt. % to 0.1 wt. %, 0.0001 wt. % to 0.05 wt. %, 0.0005 wt. % to 0.03 wt. %, 0.0005 wt. % to 0.02 wt. %, or 0.001 wt. % to 0.01 wt. %.

HCFC-243db may be present in an amount of at least 0.0001 wt. %, at least 0.0005 wt. %, and at least 0.001 wt. %, and as high as 0.05 wt. %, as high as 0.02 wt. %, as high as 0.01 wt. %, as high as 0.005 wt. %, as high as 0.003 wt. %, or any combination thereof, such as 0.0001 wt. % to 0.05 wt. %, 0.0005 wt. % to 0.02 wt. %, 0.001 wt. % to 0.01 wt. %, or 0.0015 wt. % to 0.005 wt. %.

The total sum of heavy components non-exclusively including chlorohexafluorobutene (HFO-1326 isomers), hexafluorobutene (HFO-1336 isomers), pentafluorobutene (HFO-1345 isomers), heptafluorobutene (HFO-1327 isomers), tetrafluorohexane (HFC-5-11-4 isomers), 1,3,3,3-tetrafluoropropane (HFC-254fb), chlorohexafluorobutane (HFC-346 isomers), octafluoropentane (HFC-458 isomers), octafluorohexene, 2,2-dichloro-1,1,1-trifluoroethane (HCFC-123), (Z)-1-chloro-3,3,3-trifluoropropene (HCFO-1233zd(Z)), $C_5H_2F_{10}$ isomers, $C_6H_2F_8$ isomers, $C_6H_4F_8$ isomers, decafluorobutane ($C_4F_{10}$), $C_6H_3F_7$ isomers, $C_6H_3F_9$ isomers, dichlorodifluoropropene (HCFO-1232 isomers), trichlorotrifluoropropane (HCFC-233 isomers), $C_6H_3Cl_2F_7$ isomers, trichlorodifluoropropane (HCFC-242 isomers), $C_8H_3F_7$ isomers, and tars may be at least 0.0005 wt. %, at least 0.001 wt. %, and at least 0.0015 wt. %, and as high as 5.0 wt. %, as high as 2.0 wt. %, as high as 1.0 wt. %, as high as 0.5 wt. %, as high as 0.3 wt. %, as high as 0.1 wt. %, or any combination thereof, such as 0.0005 wt. % to 2.0 wt. %, 0.0005 wt. % to 1.0 wt. %, 0.0005 wt. % to 0.5 wt. %, 0.001 wt. % to 0.3 wt. %, or 0.0015 wt. % to 0.1 wt. %.

The total amount of the impurity or combination of impurities is not particularly limited and may be present in an amount of at least 0.0001 wt. %, at least 0.0002 wt. %, and at least 0.0003 wt. %, and as high as 5.0 wt. %, as high as 3.0 wt. %, as high as 2.0 wt. %, as high as 1.0 wt. %, as high as 0.5 wt. %, or any combination thereof, such as 0.0001 wt. % to 5.0 wt. %, 0.0001 wt. % to 3.0 wt. %, 0.0001 wt. % to 2.0 wt. %, 0.0002 wt. % to 1.0 wt. %, or 0.0003 wt. % to 0.5 wt. %. For example, in some embodiments, where the composition may have two or more impurities, the total impurities may be present in the aforementioned ranges. By way of a non-limiting example, compositions may have both 253fb and 347 isomers in a combined amount that is present in an amount of at least 0.0005 wt. %, at least 0.001 wt. %, and at least 0.0015 wt. %, and as high as 0.5 wt. %, as high as 0.2 wt. %, as high as 0.1 wt. %, as high as 0.05 wt. %, as high as 0.02 wt. %, or any combination thereof, such as 0.0005 wt. % to 0.5 wt. %, 0.0005 wt. % to 0.2 wt. %, 0.001 wt. % to 0.05 wt. %, or 0.0015 wt. % to 0.02 wt. %. For one example, a composition having 0.022 wt. % of 253fb and 0.0186 wt. % of 347 would fall within the range of 0.001 wt. % to 0.05 wt. %. For another example, a composition having 0.003 wt. % of 253fb and 0.1139 wt. % of 347 would fall within the range of 0.0005 wt. % to 0.2 wt. %.

As used herein, the modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range "from about 2 to about 4" also discloses the range "from 2 to 4."

FIG. 1A is process flow diagram illustrating exemplary manufacturing process flow 1 according to various embodiments. HF feed 5 and 1233xf feed 3 (from Step 1) may be combined, for example, with any pipe or vessel, such as combination flow valves 28 and may be heated by heat exchangers 24 and then fed as stream 7 to reactor 2. In reactor 2, which may be and is shown in FIG. 1A as a liquid phase reactor, HCFC-244bb is produced as briefly described above as Step 2. After the reaction of Step 2 takes place in reactor 2, the crude HCFC-244bb product stream 9 is sent to catalyst stripper column 4, where catalysts are separated and are returned to reactor 2 in return stream 18. After processing in catalyst stripper column 4 and heat exchanger 22, the stripped crude HCFC-244bb product stream 11 is sent to lights distillation column 6. In lights distillation column 6, the light boilers are distilled off as lights overhead stream 13, while the lights bottoms stream 15 may be cooled by heat exchanger 16 and may be sent to phase separator 8 via stream 24, where HF is separated from the lights bottoms stream 15, which contains HCFC-244bb. The HF phase may then be recycled back to the Step 2 reactor as recycle HF stream 19 and the liquid stream 17 containing HCFC-244bb may be sent to one or more distillation columns.

FIG. 1A illustrates liquid stream 17 being sent first to azeotropic distillation column 10. In azeotropic distillation column 10, HCFO-1233xf may be removed from the HCFC-244bb liquid stream using azeotropic distillation. To this end, a third stream, such as unreacted reagents and/or byproducts from Step 3, may be provided by recycle stream 29 to form an azeotrope or azeotropic composition, which is then isolated from the composition. More specifically, the presence of a third component (e.g., HF) may form a ternary azeotrope and/or binary azeotropes with HCFO-1233xf, and/or HCFC-244bb. Various azeotropes may be separated from the solution using standard separation means, such as distillation in azeotropic distillation column 10, such that a significant portion of the HCFC-244bb remains in solution in azeotropic bottoms 21.

In various embodiments of this disclosure, a composition which comprises effective amounts of HF, light organics, heavy organics, or combinations thereof to form an azeotropic or azeotrope-like composition is provided. As used herein, the term "effective amount" is an amount of each component which, when combined with the other component, results in the formation of an azeotrope or azeotrope-like mixture. As used herein, the terms "heteroazeotrope" and "heterogeneous azeotrope" include an azeotrope-like compositions comprising a vapor phase existing concurrently with two liquid phases.

Such azeotropes and methods of azeotropic separation or distillation may further include those disclosed in U.S. Pat. No. 7,803,283, and U.S. Published Application Nos. 2010/0187088 and 2009/0256110, the contents of each of which are all incorporated herein by reference.

Azeotropic column bottoms 21 may then be isolated as purified HCFC-244bb in heavies distillation column 12 that may be substantially free of 253fb, and other heavy impurities, shown as purified overhead HCFC-244bb stream 27, which may be sent for further processing (e.g., Step 3) and/or stored. Azeotropic overhead stream 23 may then be recycled back to be reused in Step 2 in reactor 2 and may be combined with feed stream 7, for example, with a pipe or vessel, such as with combination flow valves 28.

Finally, bottoms 25 of heavies distillation column 12, which may contain enriched 253fb as well as tars and/or other heavy boilers, may then be collected, subjected to additional recovery to improve yield and/or disposed of. As used herein, the term "heavy boilers" may include organic compositions that have a boiling point higher than 244bb, which has a normal boiling point of about 14-15° C. For example, in some embodiments, heavy organics may have a boiling point above about 15° C. Heavy organics may include HCFC-253fb, $C_4F_{10}$, $C_5H_2F_{10}$ isomers, various tetrafluorohexane isomers, $C_6H_3F_7$ isomers, $C_6H_3Cl_2F_7$ isomers, $C_6H_2F_8$ isomers, $C_6H_4F_8$ isomers, $C_6H_3F_9$ isomers, various octafluorohexene isomers, $C_8H_3F_7$ isomers, tars, or combinations thereof.

As used herein, the term "heavy boilers" may include organic compositions that have a boiling point higher than 244bb, which has a normal boiling point of about 14-15° C. For example, in some embodiments, heavy organics may have a boiling point above about 15° C. Heavy organics may include HCFC-253fb, $C_4F_{10}$, $C_5H_2F_{10}$ isomers, various tetrafluorohexane isomers, $C_6H_3F_7$ isomers, $C_6H_3Cl_2F_7$ isomers, $C_6H_2F_8$ isomers, $C_6H_4F_8$ isomers, $C_6H_3F_9$ isomers, various octafluorohexene isomers, $C_8H_3F_7$ isomers, tars, or combinations thereof.

Figure 1B:
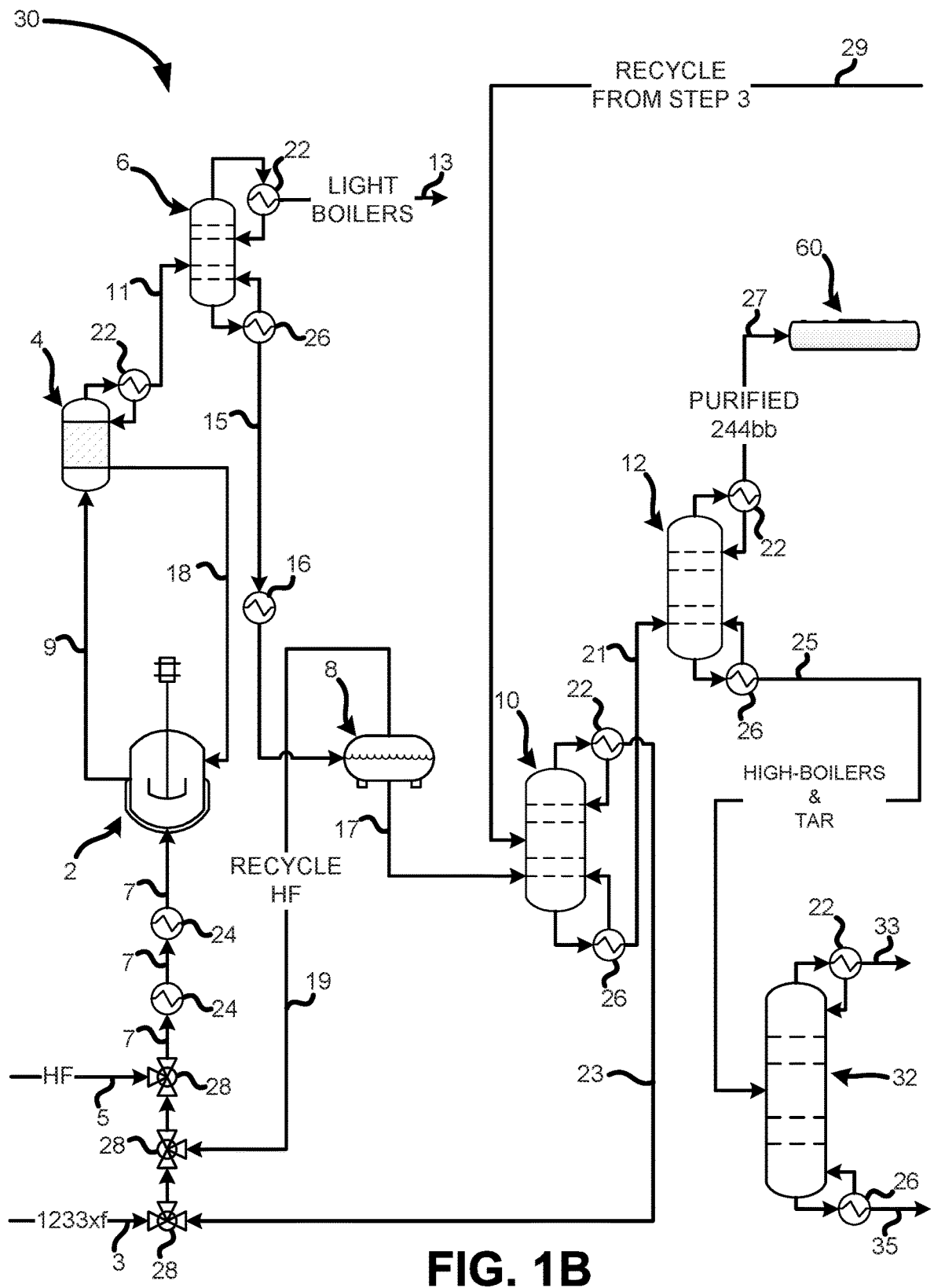
FIG. 1B is a process flow diagram similar to the process flow depicted in FIG. 1A that additionally includes a third distillation column in series.
Figure 1C:
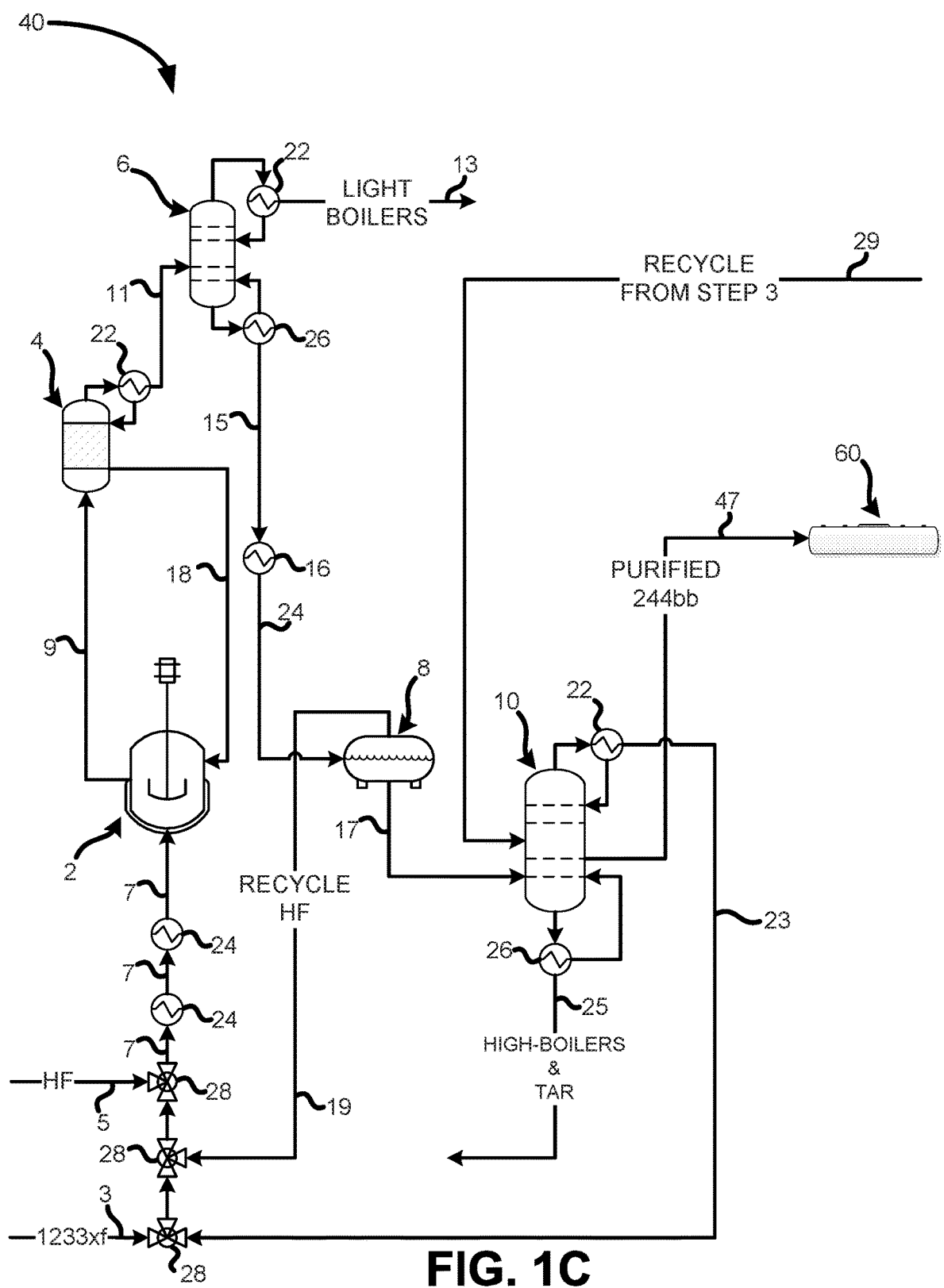
FIG. 1C is a process flow diagram similar to the process flow depicted in FIG. 1A showing an exemplary portion of a manufacturing process of 2,3,3,3-tetrafluoropropene (HFO-1234yf) using a side-draw from a distillation column.

Thus, in some embodiments, such as the process flow diagram depicted in FIGS. 1A-1C, the impurities removed may include at least one of 1-chloro-3,3,3-trifluoropropane (HCFC-253fb), 1,1,1,3,3-pentafluoropropane (HFC-245fa), heptafluorobutane (HFC-347), chlorohexafluorobutene (HFO-1326 isomers), hexafluorobutene (HFO-1336 isomers), pentafluorobutene (HFO-1345 isomers), heptafluorobutene (HFO-1327 isomers), 1-chloro-1,1,2,2-tetrafluoropropane (HCFC-244cc), 2,3-dichloro-1,1,1,2-tetrafluoropropane (HFC-234bb), chlorotetrafluoropropenes (HCFO-1224 isomers), tetrafluorohexane (HFC-5-11-4 isomers), tetrafluoropropane (HFC-254 isomers), chlorohexafluorobutane (HFC-346 isomers), octafluoropentane (HFC-458 isomers), chlorotrifluoropropene (HCFO-1233 isomers), (E)-1-chloro-3,3,3-trifluoropropene (HCFO-1233zd(E)), 2-chloro-1,1,1,3,3-pentafluoropropane (HCFC-235da), octafluorohexene, 3-chloro-1,1,1,2-tetrafluoropropane (HFC-244eb), 2,2-dichloro-1,1,1-trifluoroethane (HCFC-123), (Z)-1-chloro-3,3,3-trifluoropropene (HCFO-1233zd(Z)), $C_5H_2F_{10}$ isomer, $C_6H_2F_8$ isomer, $C_6H_4F_8$ isomer, decafluorobutane ($C_4F_{10}$), $C_6H_3F_7$ isomer, $C_6H_3F_9$ isomer, dichlorodifluoropropene (HCFO-1232 isomers), dichlorotrifluoropropene (HCFO-1223 isomers), dichlorotetrafluoropropane (HCFC-234 isomers), dichlorotrifluoropropane (HCFC-243 isomers), trichlorotrifluoropropane (HCFC-233 isomers), $C_6H_3Cl_2F_7$ isomers, trichlorodifluoropropane (HCFC-242 isomers), $C_8H_3F_7$ isomers, tars, or combinations thereof.

In some embodiments, such as process flow 30 depicted in FIG. 1B, which includes many aspects which are similar or identical to that of FIG. 1A, bottoms 25 of heavies distillation column 12 may be further separated, such as with distillation column 32. In some embodiments, heavies recovery distillation column 32 may further separate the high-boilers and tar from heavies distillation column 12 into overhead 33 and bottoms 35. In various embodiments, heavies recovery distillation column 32 may operate by batch distillation and in other embodiments, distillation column 32 may operate by continuous distillation. Also, in some embodiments, the purified 244bb or partially purified 244bb may be stored in a storage container, such as storage container 60.

In some embodiments, such as process flow 40 depicted in FIG. 1C, which includes many aspects which are similar or identical to that of FIG. 1A, illustrates the separation of purified 244bb using a side-draw 47 off of distillation column 10. In some embodiments, the use of a side-draw may be beneficial due to the separation differences within the various trays of distillation column 10 due to the vapor pressure differences between the high-boilers and tar and the purified 244bb.

Distillation column 12 in FIG. 1A-1C and 32 in FIG. 1B can be operated in batch or continuous mode. The conditions of these columns depend, to a certain extent, on utilities used as well as cost of both operation and equipment. Distillation column 12 and/or distillation column 32 is operated to achieve the optimum separation of 244bb from the impurities using conventional distillation, and/or series of distillations. Exemplary processes include decanting, centrifuging, liquid-liquid extraction, distilling, flash distilling, partial vaporization, partial condensing, or combinations thereof.

Such compositions may be useful in the production of 2,3,3,3-tetrafluoropropene (1234yf). For example, FIG. 2 illustrates process flow diagram 70 showing the production of 1234yf from a feed containing a purified 244bb and at least one impurity. Process flow diagram 70 of FIG. 2 includes an input stream 27 containing HCFC-244bb, which may contain the at least one of the aforementioned impurities, as exemplified in the description of FIGS. 1A and 1B.

The composition containing HCFC-244bb and at least one of the aforementioned impurities may then be heated by heat exchanger 24 and sent to dehydrochlorinating reactor 72 to produce 1234yf (Step 3 as briefly described above). The reacted product stream 75 containing the 1234yf may then be sent to recycle column 62, where bottoms 63 may be recycled back to reactor 72 and/or back to Step 2 azeotropic distillation column 10 as stream 29 in FIGS. 1A and 1B, and overhead 65 may be sent to be scrubbed with HCl stream 67 in HCl column 64. The HCl scrubbed stream 69 may then scrubbed with solution stream 77 in scrubber 74. The solution stream 77 is not particularly limited and may be water or a solution, such as a caustic solution or an acidic solution, such as a solution containing sulfuric acid. The scrubbed product stream 79 may then be sent to drier 76 to remove any scrubbing solution that may remain.

The dried product stream 81 may then be distilled in lights distillation column 78, where overhead lights stream 83 is passed through heat exchanger 22 and recycled or removed. Lights bottoms stream 85 may be heated or cooled via heat exchanger 26 and may be further distilled in product distillation column 80. Purified 1234yf stream 87 may be processed through heat exchanger 22 and may be stored in container 82 and/or recycled. Product bottoms stream 29 may be heated with heat exchanger 26 and may be recycled back into product distillation column 80 and/or may be removed for disposal.

Dehydrochlorination of HCFC-244bb may be carried out at a temperature range of 200° C. to 800° C., preferably from 300° C. to 600° C., and more preferably from 425° C. to 525° C., and at a pressure range of 0 to 300 psig, preferably from 5 to 200 psig, and more preferably from 20 to 100 psig. Residence time of the HCFC-244bb in reactor may range from about 1 second to about 320 seconds, however, longer or shorter times can be used.

Example

A unit comprising all the unit operations as described in FIG. 1A was operated for a month. During the operation, organic samples were daily taken from process streams 17, 21, and 27 for GC and GCMS analysis. Table 1 presents the average organic compositions of these three streams.

TABLE 1

| Component | GC area % | | |
|---|---|---|---|
| | Stream 17 | Stream 21 | Stream 27 |
| Other lights[1] | 0.1911 | 0.0055 | 0.0024 |
| 2-chloro-3,3,3-trifluoropropene (HCFO-1233xf) | 2.7058 | 1.3329 | 1.3941 |
| 2-chloro-1,1,1,2-tetrafluoropropane (HCFC-244bb) | 95.5392 | 98.1288 | 98.2937 |
| 1-chloro-1,1,2,2-tetrafluoropropane (HCFC-244cc) | 0.0821 | 0.0939 | 0.0956 |
| Chlorotetrafluoropropene (HCFO-1224 isomer) | 0.0005 | 0.0010 | 0.0009 |
| E-1-chloro-3,3,3-trifluoropropene (HCFO-1233zdE) | 0.0021 | 0.0094 | 0.0104 |
| 1,1,1,3,3-pentafluoropropane (HFC-245fa) | 0.8793 | 0.0087 | 0.0072 |

TABLE 1-continued

| | GC area % | | |
|---|---|---|---|
| Component | Stream 17 | Stream 21 | Stream 27 |
| Heptafluorobutane (HFC-347 isomer) | 0.0186 | 0.1135 | 0.1139 |
| 2-chloro-1,1,1,3,3-pentafluoropropane (HFC-235da) | 0.0019 | 0.0036 | 0.0014 |
| 3-chloro-1,1,1,2-tetrafluoropropane (HCFC-244eb) | 0.0210 | 0.0150 | 0.0024 |
| 3-chloro-3,3,3-trifluoropropane (HCFC-253fb) | 0.0220 | 0.0132 | 0.0030 |
| Dichlorotrifluoropropene (HCFO-1223 isomer) | 0.0117 | 0.0072 | 0.0005 |
| 2,3-dichloro-1,1,1,2-tetrafluoropropane (HCFC-234bb) | 0.0495 | 0.0276 | 0.0020 |
| 2,2-dichloro-1,1,1-trifluoropropane (HCFC-243db) | 0.0193 | 0.0100 | 0.0014 |
| Other heavies | 0.4559 | 0.2298 | 0.0711 |

[1] In addition to 1233xf, non-limiting examples of other lights include 2,3,3,3-tetrafluoropropene(HFO-1234yf), pentafluoropropene (HFO-1225ye isomer(s)), 1,3,3,3-tetrafluoropropene (HFO-1234ze isomer(s)), 1,1,1,2,2-pentafluoropropane (HFC-245cb), and 1,1,1,2-tetrafluoropropane (HFC-254eb).

[2] In addition to those listed in Table 1 after 244bb component, non-limiting examples of other heavies include chlorohexafluorobutene (HFO-1326 isomers), hexafluorobutene (HFO-1336 isomers), pentafluorobutene (HFO-1345 isomers), heptafluorobutene (HFO-1327 isomers), tetrafluorohexane (HFC-5-11-4 isomers), 1,3,3,3-tetrafluoropropane (HFC-254fb), chlorohexafluorobutane (HFC-346 isomers), octafluoropentane (HFC-458 isomers), octafluorohexene, 2,2-dichloro-1,1,1-trifluoroethane (HCFC-123), (Z)-1-chloro-3,3,3-trifluoropropene (HCFO-1233zd(Z)), $C_5H_2F_{10}$ isomers, $C_6H_2F_8$ isomers, $C_6H_4F_8$ isomers, decafluorobutane ($C_4F_{10}$), $C_6H_3F_7$ isomers, $C_6H_3F_9$ isomers, dichlorodifluoropropene (HCFO-1232 isomers), trichlorotrifluoropropane (HCFC-233 isomers), $C_6H_3Cl_2F_7$ isomers, trichlorodifluoropropane (HCFC-242 isomers), $C_8H_3F_7$ isomer, and tars.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements. The scope is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art with the benefit of the present disclosure to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. § 112(f), unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A composition comprising:
2-chloro-1,1,1,2-tetrafluoropropane (HCFC-244bb), and
at least one impurity comprising at least one of: 1-chloro-1,1,2,2-tetrafluoropropane (HCFC-244cc), 1,1,1,3,3-pentafluoropropane (HFC-245fa) in an amount from 0.0005 wt. % to 1.0 wt. %, 2-chloro-1,1,1,3,3-pentafluoropropane (HFC-235da), 3-chloro-1,1,1,2-tetrafluoropropane (HCFC-244eb), 2,3-dichloro-1,1,1,2-tetrafluoropropane (HCFC-234bb), and 2,2-dichloro-1,1,1-trifluoropropane (HCFC-243db) in an amount from 0.0001 wt. % to 0.05 wt. %.

2. The composition of claim 1, wherein the at least one impurity is present in an amount from about 0.0001 wt. % to about 2.0 wt. %.

3. The composition of claim 2, wherein the at least one impurity is present in an amount from about 0.0005 wt. % to about 0.5 wt. %.

4. The composition of claim 3, wherein the at least one impurity is present in an amount from about 0.001 wt. % to about 0.05 wt. %.

5. The composition of claim 1, wherein the composition comprises at least two different impurities.

6. The composition of claim 1, wherein the HCFC-244bb is present in an amount between 95 wt. % to 99.999 wt. %.

7. The composition of claim 1, wherein the HCFC-244bb is present in an amount between 98.0 wt. % to 99.0 wt. %.

8. The composition of claim 1, wherein the at least one impurity includes 1,1,1,3,3-pentafluoropropane (HFC-245fa) in an amount from 0.0005 wt. % to 0.5 wt. %.

9. The composition of claim 1, wherein the at least one impurity includes 1-chloro-1,1,2,2-tetrafluoropropane (HCFC-244cc) in an amount from 0.0005 wt. % to 0.5 wt. %.

10. The composition of claim 9, wherein the 1-chloro-1,1,2,2-tetrafluoropropane (HCFC-244cc) is in an amount from 0.001 wt. % to 0.2 wt. %.

11. The composition of claim 1, wherein the at least one impurity includes 2-chloro-1,1,1,3,3-pentafluoropropane (HFC-235da) in an amount from 0.0001 wt. % to 0.02 wt. %.

12. The composition of claim 11, wherein the 2-chloro-1,1,1,3,3-pentafluoropropane (HFC-235da) is in an amount from 0.0001 wt. % to 0.01 wt. %.

13. The composition of claim 1, wherein the at least one impurity includes 3-chloro-1,1,1,2-tetrafluoropropane (HCFC-244eb) in an amount from 0.0001 wt. % to 0.05 wt. %.

14. The composition of claim 13, wherein the 3-chloro-1,1,1,2-tetrafluoropropane (HCFC-244eb) is in an amount from 0.0001 wt. % to 0.03 wt. %.

15. The composition of claim 1, wherein the at least one impurity includes 2,2-dichloro-1,1,1-trifluoropropane (HCFC-243db) in an amount from 0.0005 wt. % to 0.02 wt. %.

16. The composition of claim 15, wherein the 2,2-dichloro-1,1,1-trifluoropropane (HCFC-243db) is in an amount from 0.001 wt. % to 0.01 wt. %.

17. The composition of claim 1, wherein the at least one impurity includes 2,3-dichloro-1,1,1,2-tetrafluoropropane (HCFC-234bb) in an amount from 0.0001 wt. % to 0.1 wt. %.

18. The composition of claim 17, wherein the 2,3-dichloro-1,1,1,2-tetrafluoropropane (HCFC-234bb) is in an amount from 0.0001 wt. % to 0.05 wt. %.

19. The composition of claim 1, wherein the at least one impurity comprises at least one of: 1,1,1,3,3-pentafluoropropane (HFC-245fa) in an amount from 0.0005 wt. % to 1.0 wt. %, 2-chloro-1,1,1,3,3-pentafluoropropane (HFC-235da), and 2,3-dichloro-1,1,1,2-tetrafluoropropane (HCFC-234bb).

20. The composition of claim 1, wherein the composition comprises the impurities: 1,1,1,3,3-pentafluoropropane (HFC-245fa), 2-chloro-1,1,1,3,3-pentafluoropropane (HFC-235da), and 2,3-dichloro-1,1,1,2-tetrafluoropropane (HCFC-234bb).

* * * * *